(12) United States Patent
Jaiswal et al.

(10) Patent No.: US 12,012,583 B2
(45) Date of Patent: Jun. 18, 2024

(54) SIX-SAMPLE UNIVERSAL MECHANICAL STIMULATION DEVICE FOR SOFT TISSUE

(71) Applicant: Western New England University, Springfield, MA (US)

(72) Inventors: Devina Jaiswal, Glastonbury, CT (US); Brennen Zolnoski, Brattleboro, VT (US); Emily Fernschild, Milford, CT (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 449 days.

(21) Appl. No.: 17/176,577

(22) Filed: Feb. 16, 2021

(65) Prior Publication Data

US 2021/0253992 A1    Aug. 19, 2021

Related U.S. Application Data

(60) Provisional application No. 62/978,461, filed on Feb. 19, 2020.

(51) Int. Cl.
| | |
|---|---|
| *C12M 1/42* | (2006.01) |
| *C12M 1/00* | (2006.01) |
| *C12M 1/32* | (2006.01) |
| *C12M 3/06* | (2006.01) |

(52) U.S. Cl.
CPC ............ *C12M 35/02* (2013.01); *C12M 23/12* (2013.01); *C12M 23/38* (2013.01); *C12M 27/14* (2013.01)

(58) Field of Classification Search
CPC ...... C12M 35/00; C12M 35/02; C12M 35/04; C12M 23/12; C12M 23/38; C12M 23/34; C12M 27/14; C12M 37/04
See application file for complete search history.

(56) References Cited

FOREIGN PATENT DOCUMENTS

EP    2130904 A2 * 12/2009 ............ C12M 23/38

OTHER PUBLICATIONS

Bogdan et al., "Dynamic Bioreactors with Integrated Microfabricated Devices forMechanobiological Screening", Tissue Engineering Part C: Methods, vol. 25, No. 10, Oct. 10, 2019, Mary Ann Liebert, Inc. publishers, pp. 3-5.*

(Continued)

*Primary Examiner* — Elizabeth A Robinson
*Assistant Examiner* — Jonathan E Lepage
(74) *Attorney, Agent, or Firm* — CANTOR COLBURN LLP

(57) ABSTRACT

A bioreactor configured for stimulation of a plurality of samples includes a well plate containing a plurality of chambers and a cover placed over the well plate. A plurality of fixed arms are located in the cover, each chamber of the plurality of chambers having a fixed arm located therein. A plurality of moving arms are located in the cover, each chamber of the plurality of chambers having a moving arm located therein. The moving arm and fixed arm of each chamber hold a sample therebetween. A moving arm shaft is located in the cover, and is operably connected to the plurality of moving arms. An electrical motor is located outside of the cover and is operably connected to the moving arm shaft. The electrical motor is configured to drive movement of the plurality of moving arms relative to the plurality of fixed arms via the moving arm shaft.

19 Claims, 3 Drawing Sheets

(56) References Cited

OTHER PUBLICATIONS

Cook at. al., "Characterization of a Novel Bioreactor System for 3D Cellular Mechanobiology Studies", Biotechnology and Bioengineering, vol. 113, No. 8, Feb. 29, 2016, Wiley Periodicals, Inc., pp. 1826-1827.*

Lei, Ying, "Development of a Biaxial Stretch Bioreactor and Finite Element Models for Mechanobiological Stufy of Aortic Valve Leaflets", PhD diss., University of Tennessee, Dec. 2017, p. 81.*

* cited by examiner

SIX-SAMPLE UNIVERSAL MECHANICAL STIMULATION DEVICE FOR SOFT TISSUE

CROSS-REFERENCE TO RELATED APPLICATIONS

This application claims the benefit of 62/978,461 filed Feb. 19, 2020, the disclosure of which is incorporated herein by reference in its entirety.

BACKGROUND

Exemplary embodiments disclosed herein relate to the art of bioreactors.

A bioreactor refers to a system or vessel in which cells or tissues are grown for cell culture and/or testing. Bioreactors often utilize a chamber, or incubator in which tissue samples are placed, submerged in a well with cell culture media. It is desired to apply uniaxial or multi-axial strain to cells via an electromechanical device to stimulate growth in the well. The humid environment of the bioreactor, however, may be damaging to electrical components of the electromechanical device.

The art would welcome a bioreactor device in which mechanical strain is applied to the cells without damage to an electrical system powering the agitation.

BRIEF DESCRIPTION

In one embodiment, a bioreactor configured for stimulation of a plurality of samples includes a well plate containing a plurality of chambers and a cover placed over the well plate. A plurality of fixed arms are located in the cover, each chamber of the plurality of chambers having a fixed arm located therein. A plurality of moving arms are located in the cover, each chamber of the plurality of chambers having a moving arm located therein. The moving arm and fixed arm of each chamber are configured to hold a sample therebetween. A moving arm shaft is located in the cover, the moving arm shaft operably connected to the plurality of moving arms. An electrical motor is located outside of the cover and is operably connected to the moving arm shaft. The electrical motor is configured to drive movement of the plurality of moving arms relative to the plurality of fixed arms via the moving arm shaft.

Additionally or alternatively, in this or other embodiments one or more longitudinal arm supports are located in the cover extending along a lengthwise axis of the cover. The plurality of fixed arms are secured to the one or more longitudinal arm supports. The plurality of moving arms are slidably positioned at the one or more longitudinal arm supports.

Additionally or alternatively, in this or other embodiments the moving arm shaft moves along the lengthwise axis to urge movement of the plurality of moving arms along the one or more longitudinal arm supports.

Additionally or alternatively, in this or other embodiments each moving arm includes an arm opening, a longitudinal arm support of the one or more longitudinal arm supports extending through the arm opening.

Additionally or alternatively, in this or other embodiments each fixed arm of the plurality of fixed arms and each moving arm of the plurality of moving arms includes a clamping device configured to hold the sample.

Additionally or alternatively, in this or other embodiments a plurality of vertical arm supports are fixed to the cover. Each vertical arm support of the plurality of vertical arm supports is secured to a fixed arm of the plurality of fixed arms.

Additionally or alternatively, in this or other embodiments a volume of cell culture is located in each chamber of the plurality of chambers.

Additionally or alternatively, in this or other embodiments a coupling portion is located outside of the cover, the coupling portion operably connecting the electrical motor to the moving arm shaft.

Additionally or alternatively, in this or other embodiments the coupling portion converts rotational motion of the electrical motor into a linear motion of the moving arm shaft.

Additionally or alternatively, in this or other embodiments the plurality of chambers are arranged in two or more rows.

In another embodiment, a bioreactor includes a housing including a plurality of chambers, and a housing cover to vertically enclose the housing. A plurality of fixed arms are located in the housing, each chamber of the plurality of chambers having a fixed arm located therein. A plurality of moving arms are located in the housing, each chamber of the plurality of chambers having a moving arm located therein. The moving arm and fixed arm of each chamber are configured to hold a sample therebetween. A moving arm shaft is located in the housing, the moving arm shaft operably connected to the plurality of moving arms. An electrical motor is located outside of the housing and is operably connected to the moving arm shaft. The electrical motor is configured to drive movement of the plurality of moving arms relative to the plurality of fixed arms via the moving arm shaft. A coupling portion is located outside of the housing and is operably connecting the electrical motor to the moving arm shaft.

Additionally or alternatively, in this or other embodiments one or more longitudinal arm supports are located in the housing and extend along a lengthwise axis of the housing. The plurality of fixed arms are secured to the one or more longitudinal arm supports. The plurality of moving arms are slidably located at the one or more longitudinal arm supports.

Additionally or alternatively, in this or other embodiments wherein the moving arm shaft moves along the lengthwise axis to urge movement of the plurality of moving arms along the one or more longitudinal arm supports.

Additionally or alternatively, in this or other embodiments each moving arm includes an arm opening, a longitudinal arm support of the one or more longitudinal arm supports extending through the arm opening.

Additionally or alternatively, in this or other embodiments the one or more longitudinal arm supports and the moving arm shaft extends through an end wall of the housing cover.

Additionally or alternatively, in this or other embodiments removal of the cover from the housing removed the plurality of fixed arms and the plurality of moving arms from the plurality of chambers.

Additionally or alternatively, in this or other embodiments a plurality of vertical arm supports are fixed to the housing cover, each vertical arm support of the plurality of vertical arm supports secured to a fixed arm of the plurality of fixed arms.

Additionally or alternatively, in this or other embodiments a volume of cell culture is located in each chamber of the plurality of chambers.

Additionally or alternatively, in this or other embodiments the coupling portion converts rotational motion of the electrical motor into a linear motion of the moving arm shaft.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
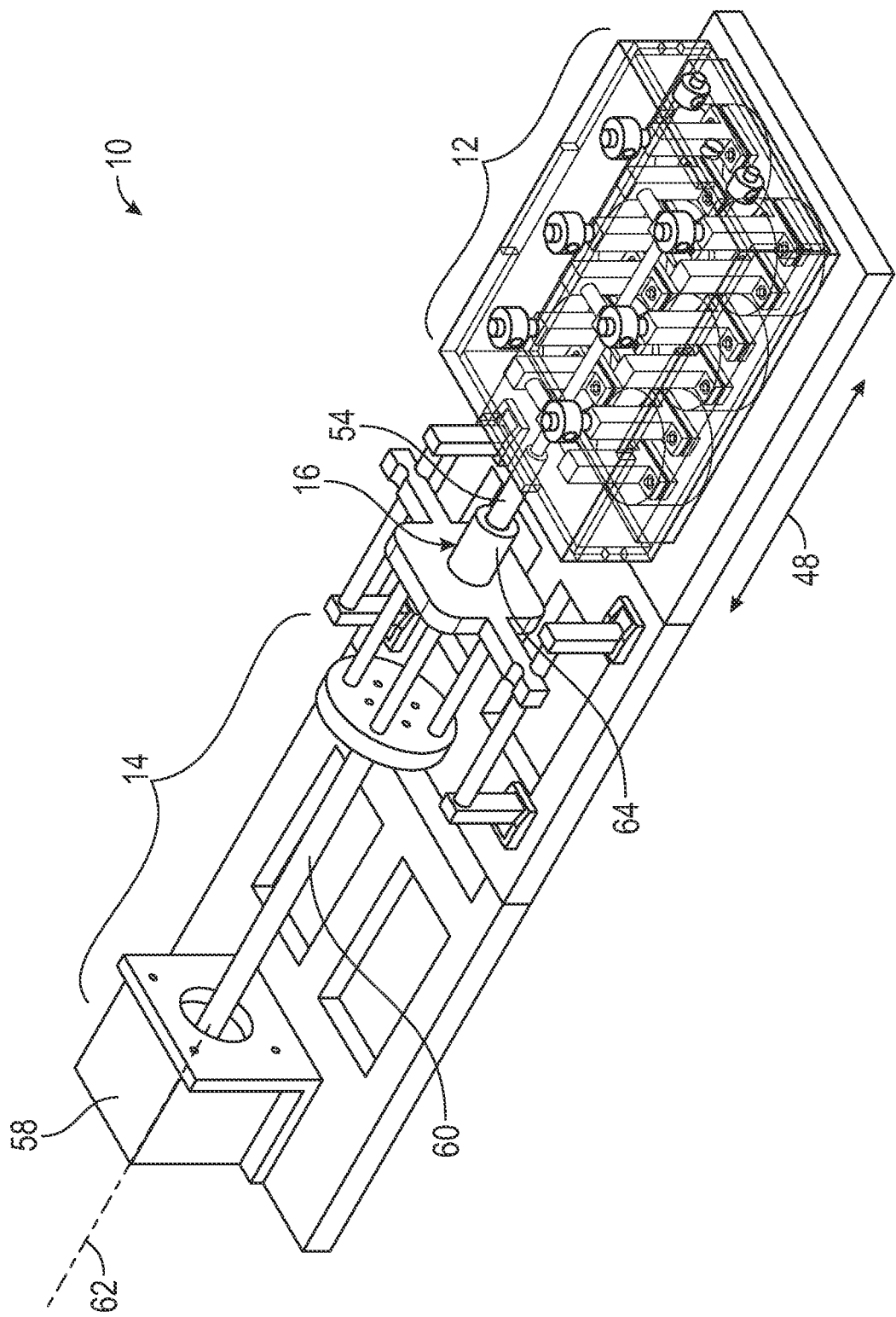
FIG. 1 is a perspective view of an embodiment of a bioreactor system.

Illustrated in FIG. 1 is an embodiment of a bioreactor system 10. The bioreactor system 10 includes a mechanical portion 12 and an electrical portion 14 connected to the mechanical portion 12 via a coupling portion 16.

Figure 2:
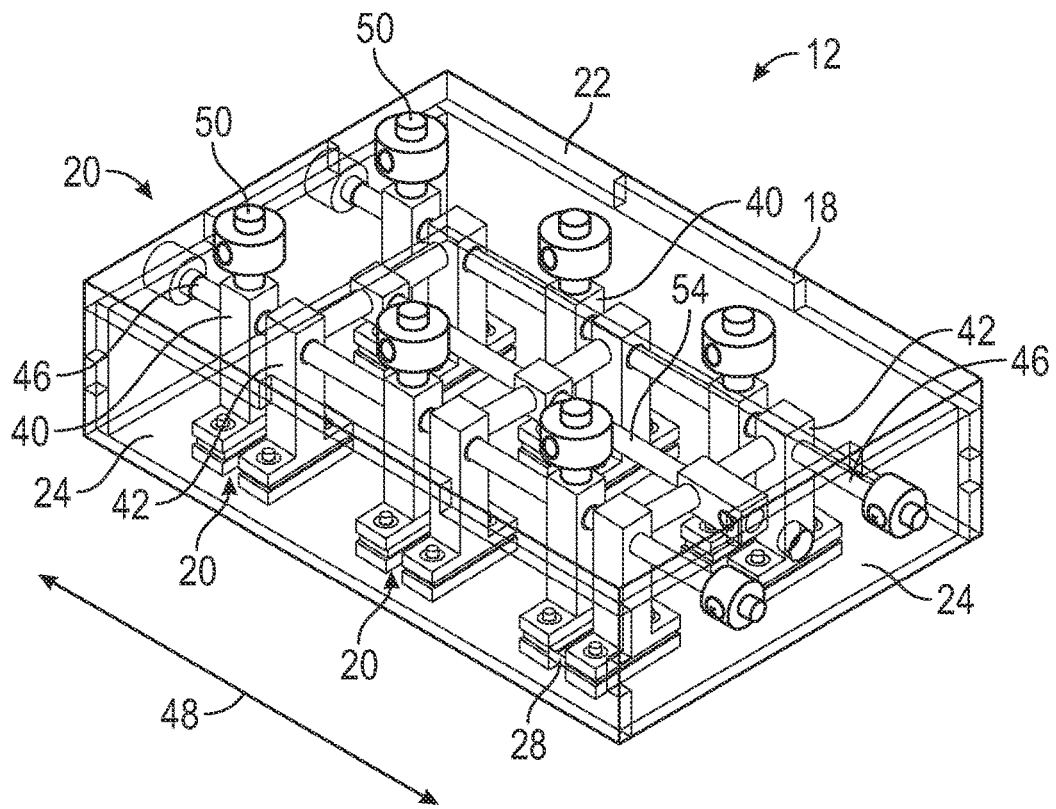
FIG. 2 is a perspective view of a mechanical portion of an embodiment of a bioreactor.
Figure 3:
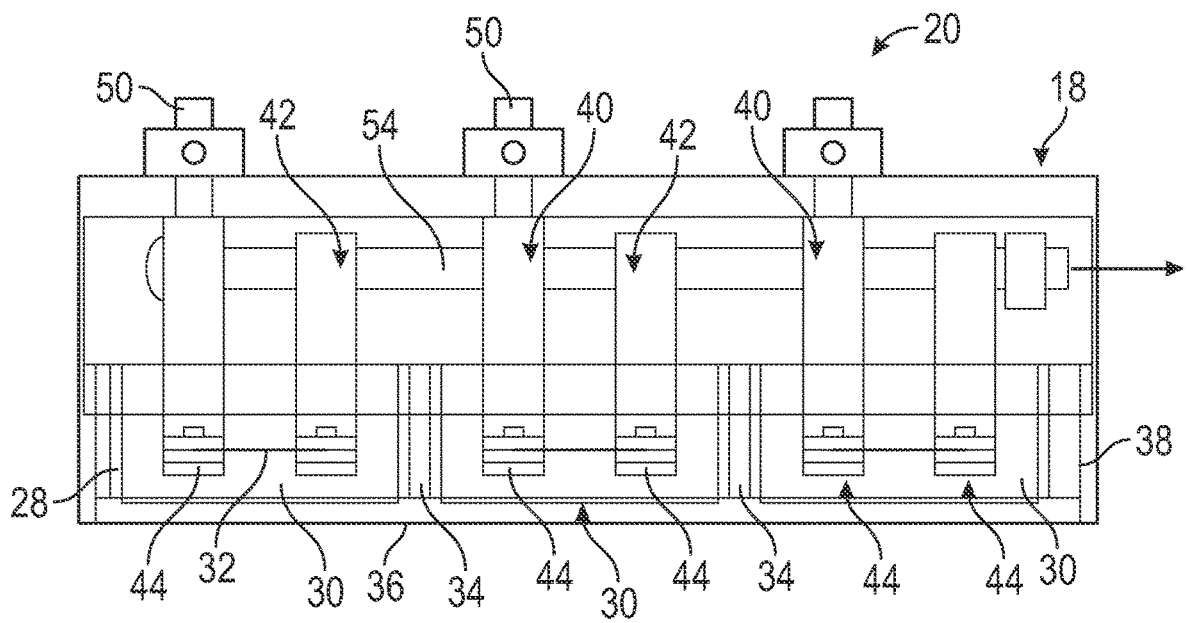
FIG. 3 is an elevation view of an embodiment of a mechanical portion of a bioreactor system.

Referring now to FIG. 2, the mechanical portion 12 includes a cover 18 and a mechanical stimulation assembly 20 retained in the cover 18. The cover 18 includes a top 22 and four side walls 24. As shown in FIG. 3, the cover 18 is positioned over a well plate 28. The well plate 28 includes a plurality of chambers 30 or wells. A plurality of samples 32, typically organic tissue, are located therein, with a sample 32 located in each of the chambers 30. In some embodiments, the well plate 28 includes six chambers 30 arranged in two rows of three chambers 30, but one skilled in the art will readily appreciate that the well plate 28 may include other quantities of chambers 30, for example, four, eight or ten chambers 30, and other arrangements may be utilized. The chambers 30, or wells, are separated by chamber walls 34, extending upwardly from a floor 36 of the well plate 28, and the chambers 30 are at least partially filled with a cell culture media 38. The cover 18 encloses the well plate 28 and prevents contamination of the samples 32 during a period of study.

The samples 32 are held in the chambers 30 by the mechanical stimulation assembly 20. In some embodiments, the mechanical stimulation assembly 20 is attached to the cover 18 such that when the cover 18 is removed from the well plate 28, the mechanical stimulation assembly 20 is also removed from the well plate 28.

Figure 4:
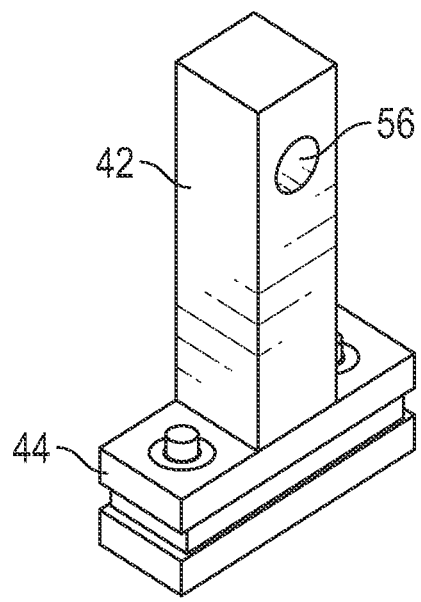
FIG. 4 is an illustration of an embodiment of a clamping device of a bioreactor.

The mechanical stimulation assembly 20 includes a plurality of fixed arms 40 and a plurality of moving arms 42. A fixed arm 40 and a moving arm 42 extends into each chamber 30 to hold a sample 32 therein. Referring to FIG. 4, each of the fixed arms 40 and each of the moving arms 42 includes a clamping device 44 to hold the sample 32. As shown in FIG. 3, the sample 32 extends between a clamping device 44 of the fixed arm 40 and a clamping device 44 of the moving arm 42. The clamping device 44 may accommodate soft tissue as well as seeded biomaterials, for example. In each chamber 30, the moving arm 42 is movable relative to the fixed arm 40 within the chamber 30 to stimulate the sample 32.

Referring again to FIG. 2, the fixed arms 40 have a fixed relationship with respect to the cover 18, and in some embodiments are connected to the cover 18 via one or more arm supports. The arm supports may include, for example, longitudinal arm supports 46 extending along a length axis 48 of the cover 18, and vertical arm supports 50 extending upwardly from the fixed arms 40 through the cover 18. In some embodiments the longitudinal arm supports 46 are two longitudinal arm supports 46, each connected to three fixed arms 40.

Figure 5:
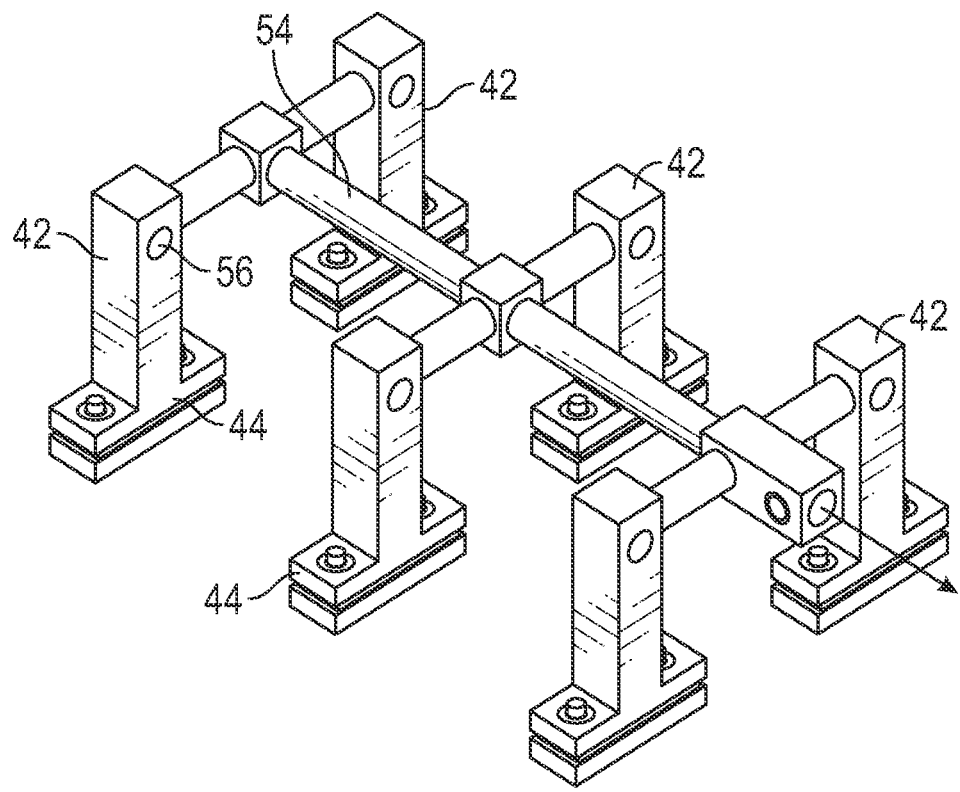
FIG. 5 is a schematic illustration of a moving arm assembly of a bioreactor.

The moving arms 42 are movable relative to the fixed arms 40, for example, along the length axis 48. Referring now to FIG. 5, the moving arms 42 are collectively connected to a moving arm shaft 54. Further, each of the moving arms 42 may have an arm opening 56 through which the longitudinal arm supports 46 extend. The moving arms 42 are thus slidable along the longitudinal arm supports 46.

Referring again to FIG. 1, the electrical portion 14 includes an electrical motor 58 and a motor shaft 60 operably connected to the electrical motor 58 and driven by the electrical motor 58 about a motor axis 62. The motor shaft 60 is operably connected to the moving arm shaft 54 via the coupling portion 16. The coupling portion 16 converts the rotational motion of the motor shaft 60 about the motor axis 62 to linear motion of the moving arm shaft 54 along the length axis 48. In some embodiments, the length axis 48 is parallel to the motor axis 62. The coupling portion 16 may include a quick release mechanism 64 to allow for quick connection and/or disconnection of the moving arm shaft 54 to or from the coupling portion 16 and thus to or from the electrical portion 14.

The bioreactor system 10 disclosed herein isolates the electrical portion 14 from the humid environment of the well plate 28, thus extending the service life of the electrical portion 14. Further, the quick release mechanism 64 allows for multiplexing of the bioreactor systems 10, such that multiple mechanical stimulation assemblies 32 may be driven by a single electrical portion 14 and electrical motor 58. Thus, system 10 cost can be reduced.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A bioreactor configured for stimulation of a plurality of samples, comprising:
 a well plate containing a plurality of chambers;
 a cover placed over the well plate;
 a mechanical stimulation assembly attached to the cover, including:
  a plurality of fixed arms connected to the cover and fixed in position relative to the cover, each chamber of the plurality of chambers having a fixed arm disposed therein;
  a plurality of moving arms disposed in the cover, each chamber of the plurality of chambers having a moving arm disposed therein, the moving arm and fixed arm of each chamber configured to hold a sample therebetween;
  a moving arm shaft disposed in the cover, the moving arm shaft operably connected to the plurality of moving arms;
  wherein the mechanical stimulation assembly is connected to the cover, such that when the cover is removed from the well plate, the plurality of fixed arms, the plurality of moving arms, and the moving arm shaft are also removed from the well plate; and
 an electrical motor disposed outside of the cover and operably connected to the moving arm shaft, the electrical motor configured to drive movement of the plurality of moving arms relative to the plurality of fixed arms via the moving arm shaft.

2. The bioreactor of claim 1, further comprising one or more longitudinal arm supports disposed in the cover extending along a lengthwise axis of the cover, the plurality of fixed arms secured to the one or more longitudinal arm supports, the plurality of moving arms slidably disposed at the one or more longitudinal arm supports.

3. The bioreactor of claim 2, wherein the moving arm shaft moves along the lengthwise axis to urge movement of the plurality of moving arms along the one or more longitudinal arm supports.

4. The bioreactor of claim 2, wherein each moving arm includes an arm opening, a longitudinal arm support of the one or more longitudinal arm supports extending through the arm opening.

5. The bioreactor of claim 1, wherein each fixed arm of the plurality of fixed arms and each moving arm of the plurality of moving arms includes a clamping device configured to hold the sample.

6. The bioreactor of claim 1, further comprising
 a plurality of vertical arm supports fixed to the cover, each vertical arm support of the plurality of vertical arm supports secured to a fixed arm of the plurality of fixed arms.

7. The bioreactor of claim 1, further comprising a volume of cell culture disposed in each chamber of the plurality of chambers.

8. The bioreactor of claim 1, further comprising a coupling portion disposed outside of the cover, the coupling portion operably connecting the electrical motor to the moving arm shaft.

9. The bioreactor of claim 8, wherein the coupling portion converts rotational motion of the electrical motor into a linear motion of the moving arm shaft.

10. The bioreactor of claim 1, wherein the plurality of chambers are arranged in two or more rows.

11. A bioreactor comprising:
 a housing including:
  a plurality of chambers; and
  a housing cover to vertically enclose the housing;
 a mechanical stimulation assembly attached to the housing cover, including:
  a plurality of fixed arms disposed in the housing and fixed to the housing cover, each chamber of the plurality of chambers having a fixed arm disposed therein;
  a plurality of moving arms disposed in the housing, each chamber of the plurality of chambers having a moving arm disposed therein, the moving arm and fixed arm of each chamber configured to hold a sample therebetween;
  a moving arm shaft disposed in the housing, the moving arm shaft operably connected to the plurality of moving arms;
  wherein the mechanical stimulation assembly is connected to the housing cover, such that when the cover is removed from the housing, the plurality of fixed arms, the plurality of moving arms, and the moving arm shaft are also removed from the housing;
 an electrical motor disposed outside of the housing and operably connected to the moving arm shaft, the electrical motor configured to drive movement of the plurality of moving arms relative to the plurality of fixed arms via the moving arm shaft; and
 a coupling portion disposed outside of the housing and operably connecting the electrical motor to the moving arm shaft.

12. The bioreactor of claim 11, further comprising one or more longitudinal arm supports disposed in the housing extending along a lengthwise axis of the housing, the plurality of fixed arms secured to the one or more longitudinal arm supports, the plurality of moving arms slidably disposed at the one or more longitudinal arm supports.

13. The bioreactor of claim 12, wherein the moving arm shaft moves along the lengthwise axis to urge movement of the plurality of moving arms along the one or more longitudinal arm supports.

14. The bioreactor of claim 12, wherein each moving arm includes an arm opening, a longitudinal arm support of the one or more longitudinal arm supports extending through the arm opening.

15. The bioreactor of claim 12, wherein the one or more longitudinal arm supports and the moving arm shaft extends through an end wall of the housing cover.

16. The bioreactor of claim 15, wherein removal of the cover from the housing removes the plurality of fixed arms and the plurality of moving arms from the plurality of chambers.

17. The bioreactor of claim 11, further comprising a plurality of vertical arm supports fixed to the housing cover, each vertical arm support of the plurality of vertical arm supports secured to a fixed arm of the plurality of fixed arms.

18. The bioreactor of claim 11, further comprising a volume of cell culture disposed in each chamber of the plurality of chambers.

19. The bioreactor of claim 11, wherein the coupling portion converts rotational motion of the electrical motor into a linear motion of the moving arm shaft.

* * * * *